United States Patent [19]

Barshay et al.

[11] Patent Number: 4,928,840
[45] Date of Patent: May 29, 1990

[54] TAMPER PROOF ENCAPSULATED MEDICAMENTS

[75] Inventors: Stanley F. Barshay, Old Westbury; Peter Mayer, New York, both of N.Y.

[73] Assignee: American Home Products Corporation, New York, N.Y.

[21] Appl. No.: 834,989

[22] Filed: Feb. 25, 1986

[51] Int. Cl.⁵ .................. B65D 8/00; B65D 53/06; A61K 9/48
[52] U.S. Cl. ........................ 220/8; 206/528; 424/451
[58] Field of Search .............. 220/8, DIG. 34; 206/528, 530, 807; D28/1, 2, 3; 424/14, 15

[56] References Cited

U.S. PATENT DOCUMENTS

| | | | |
|---|---|---|---|
| 2,155,444 | 4/1939 | Pittenger | 424/14 |
| 2,584,166 | 2/1952 | Stevenson | D28/1 |
| 3,345,265 | 10/1967 | Grodberg | D28/2 |
| 3,702,653 | 11/1972 | Moffin | 206/530 |
| 4,250,997 | 2/1981 | Bodenmann | 206/528 |

Primary Examiner—George E. Lowrance
Attorney, Agent, or Firm—John W. Routh

[57] ABSTRACT

A tamper-proof capsule dosage form for pharmaceuticals having a medicinal containing caplet adhesively bonded to the inner end surfaces of the capsule such that upon tampering the capsule dosage form will be destroyed or rendered non-reusable.

1 Claim, 1 Drawing Sheet

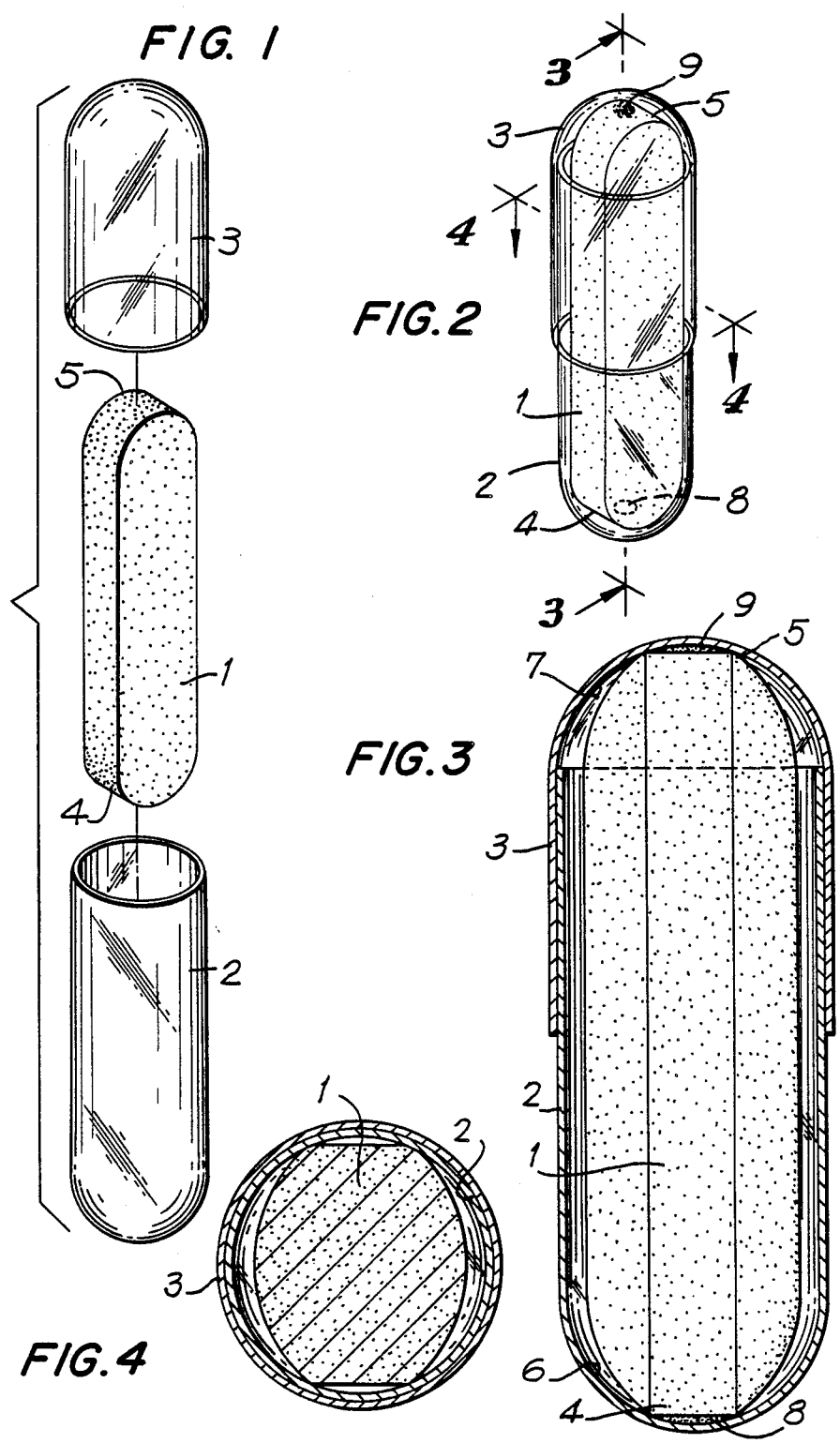

TAMPER PROOF ENCAPSULATED MEDICAMENTS

BACKGROUND OF THE INVENTION

This invention relates to a tamperproof capsule dosage form for pharmaceutical preparations and more particularly to a hard gelatin capsule dosage form which will be destroyed if opened so that extraneous substances cannot be inserted in the opened capsule and the capsule then re-closed.

The art is replete with systems for locking capsules containing pharmaceutical preparations for oral administration. For example, sound waves have been used to lock together the two pieces of hard gelatin shell after the medicament has been enclosed within the capsule formed from the shells. In another system, the larger half of the two-piece capsule fits almost completely over the smaller half. In still another system, a gelatin band is applied to the filled capsule and fused to hold the two capsule pieces together. Such systems have been found to be lacking in adequate protection, however, since one or several capsules can be opened and the components used to encapsulate an extraneous substance in capsule components closely resembling the original medication.

SUMMARY OF THE INVENTION

This invention comprises a tamper-proof capsule dosage form containing a pharmaceutical medicament for oral administration which will be destroyed if opened prior to administration. The tamper-proof capsule dosage form comprises three basic components including a hard gelatin capsule, a pharmaceutical medicament in caplet, i.e. elongated tablet shape, and an edible adhesive, which components, when assembled hold each end of the caplet adhesively bonded to the adjacent inside surface of the capsule.

DETAILED DESCRIPTION OF THE INVENTION

The three basic components of the tamper-proof capsule dosage form of the invention comprise:

(a) a hard gelatin capsule, well known in the art, such is marketed by R. P. Scherer Corporation of Troy, N.Y., made in two pieces in which the medicament, usually in powder or particulate form, is placed in a first piece and the other piece is then slip-fitted over and joined to the first piece;

(b) a medicinal caplet for oral administration shaped and sized closely to fit within the assembled capsule; and (c) a pharmaceutically acceptable edible adhesive, the adhesive bonding each end portion of the caplet to the adjacent inside surface of the capsule.

The hard gelatin capsule can be any size from 4 to 000 and preferably it should be a clear gelatin so that the user can see the caplet inside and also extraneous material, if any.

The caplet can contain any of the many medicinals presently marketed over-the-counter or on a prescription basis such as aspirin, acetaminophen and ibuprofen.

The edible adhesive can be a pharmaceutically acceptable water or organic solvent soluble adhesive including a protein adhesive such as zein or casein, a silicone adhesive, a plastic adhesive such as an acrylic polymer, shellac or a cellulose. Also the adhesive can be a heat-sealable or an ultrasound-sealable adhesive well known to the art.

The invention will now be described with reference to the accompanying drawings wherein:

FIG. 1 is an exploded view of the tamper-proof encapsulated dosage form of the invention:

FIG. 2 is a view of the assembled tamper-proof encapsulated dosage form of the invention.

FIG. 3 is a cross-sectional view along line 3—3, i.e. the elongated axis of the tamper-proof encapsulated dosage form of the invention; and FIG. 4 is a cross-sectional view along line 4—4, i.e. around the circumference of the encapsulated dosage form of the invention.

Turning now to FIGS. 1 through 4, the caplet 1 is sized closely to fit into the capsule designated by its two components 2 and 3. The caplet mold can be designed to provide sufficient tolerance such that there is sufficient space at each end 4 and 5 of the caplet 1 and between the inside surfaces 6 and 7 of the capsule ends 2 and 3 to receive a drop or two of adhesive designated 8 and 9 respectively.

The tamper-proof dosage form is assembled by placing the adhesive on each end of the caplet or on the inner end surfaces of the capsule sections, inserting the caplet into the section of the capsule smaller in diameter, then slipping the section of the capsule larger in diameter over the exposed end of the caplet and slip-fitting the two sections together to form the capsule.

Any moisture or solvent in the adhesive will pass through the capsule wall since the gelatin acts as a semipermeable membrane. If too much moisture is present in the adhesive, the capsule may become deformed, and hence it is preferable to use low moisture content adhesives. Gentle warming of the filled capsules will accelerate the drying of the adhesive.

I claim:

1. A tamper-proof capsule dosage form containing a pharmaceutical medicament for oral administration comprising:
    (a) an elongated essentially round hard gelatin capsule made in two sections slip-fit joinable;
    (b) a solid caplet containing a medicament substance shaped and sized closely to fit within the assembled capsule; and
    (c) a pharmaceutically acceptable adhesive situated between each caplet end and the adjacent inner surface of the capsule.

* * * * *